United States Patent [19]

Proto et al.

[11] Patent Number: 5,046,350

[45] Date of Patent: Sep. 10, 1991

[54] APPARATUS FOR ATTACHING SURGICAL SUTURE COMPONENTS

[75] Inventors: George R. Proto, West Haven; Francis D. Colligan, Waterbury, both of Conn.

[73] Assignee: United States Surgical Corporation, Norwalk, Conn.

[21] Appl. No.: 431,303

[22] Filed: Nov. 3, 1989

[51] Int. Cl.⁵ ............................................. B21D 37/10
[52] U.S. Cl. ...................................... 72/416; 604/273
[58] Field of Search .................. 72/360, 416; 604/272, 604/273

[56] References Cited

U.S. PATENT DOCUMENTS

| | | |
|---|---|---|
| Re. 27,735 | 8/1973 | Shave et al. . |
| Re. 31,084 | 11/1982 | Birks . |
| 1,558,037 | 10/1925 | Morton . |
| 1,578,543 | 3/1926 | Montgomery . |
| 2,067,568 | 1/1937 | Grunthal ......................... 72/416 X |
| 2,205,893 | 6/1940 | Unger . |
| 2,411,079 | 11/1946 | Baule . |
| 2,620,028 | 12/1952 | Kohut . |
| 2,958,929 | 11/1960 | Vineberg . |
| 2,983,898 | 5/1961 | Kalmar et al. . |
| 3,055,412 | 9/1962 | Dibner . |
| 3,130,489 | 4/1964 | Schlage . |
| 3,253,328 | 5/1966 | Baldwin . |
| 3,643,327 | 2/1972 | Jackson . |
| 3,771,343 | 11/1973 | Dawson . |
| 3,890,975 | 6/1975 | McGregor . |
| 3,910,282 | 10/1975 | Messer et al. . |
| 3,963,031 | 6/1976 | Hunter . |
| 3,972,219 | 8/1976 | Riehl .................................. 72/416 |
| 3,980,177 | 9/1976 | McGregor . |
| 4,054,144 | 10/1977 | Hoffman et al. . |
| 4,060,885 | 12/1977 | Hoffman et al. . |
| 4,067,224 | 1/1978 | Birks . |
| 4,072,041 | 2/1978 | Hoffman et al. . |
| 4,192,171 | 3/1980 | Hamilton . |
| 4,292,833 | 10/1981 | Lapp .................................. 72/416 |
| 4,361,948 | 12/1982 | Omata . |
| 4,498,222 | 2/1985 | Ono et al. . |
| 4,567,650 | 2/1986 | Balyasny et al. . |
| 4,719,789 | 1/1988 | Wiebe et al. . |
| 4,722,384 | 2/1988 | Matsutani . |
| 4,799,311 | 1/1989 | Matsutani . |

FOREIGN PATENT DOCUMENTS

| | | |
|---|---|---|
| 0249504 | 6/1987 | European Pat. Off. . |
| 8715099 | 3/1988 | Fed. Rep. of Germany . |
| 8715099 | 3/1988 | Fed. Rep. of Germany . |
| 3805772 | 9/1988 | Fed. Rep. of Germany . |
| 1526222 | 9/1978 | United Kingdom . |

Primary Examiner—Mark Rosenbaum
Assistant Examiner—Frances Chin
Attorney, Agent, or Firm—Peter G. Dilworth; Rocco S. Barrese; Thomas R. Bremer

[57] ABSTRACT

A pair of dies is disclosed for attaching a surgical needle having a generally cylindrical end portion defining an elongated aperture having a generally circular cross-section and a suture having a generally elongated end portion of generally circular cross-section corresponding in dimension to the elongated aperture of the first needle. Each die has a pair of extensions spaced apart from each other and defines a generally circular crimping surface portion corresponding in dimension and configuration to the generally cylindrical outer surface portion of the needle. The space defines a unique relief zone between the pair of extensions of the die and is of configuration and dimension sufficient such that when the suture is positioned within the aperture of the needle and the dies are respectively positioned about the corresponding portion of the needle, the application of impact force to the dies will cause crimping of the needle with respect to the suture so as to attach the suture and the needle while portions of material forming part of the needle adjacent the stricken area are permitted to be deformed and to collect within the relief zones defined between the pairs of arcuate surface portions. Generally arcuate die overlap portions may be optionally provided on each die. A method of attaching a surgical needle to a suture is also disclosed.

13 Claims, 4 Drawing Sheets

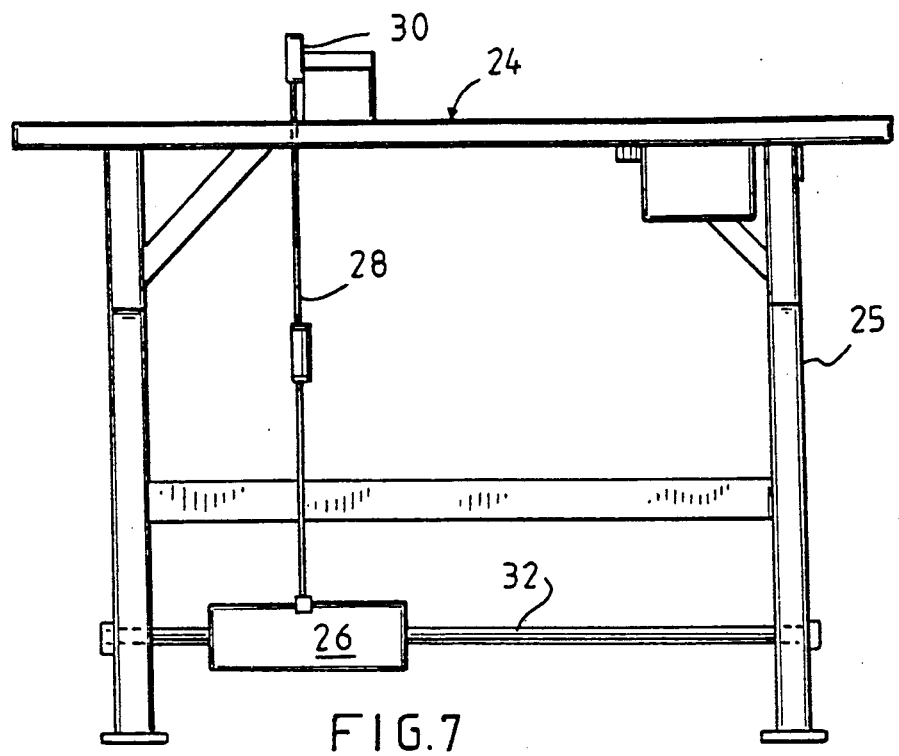
FIG.7
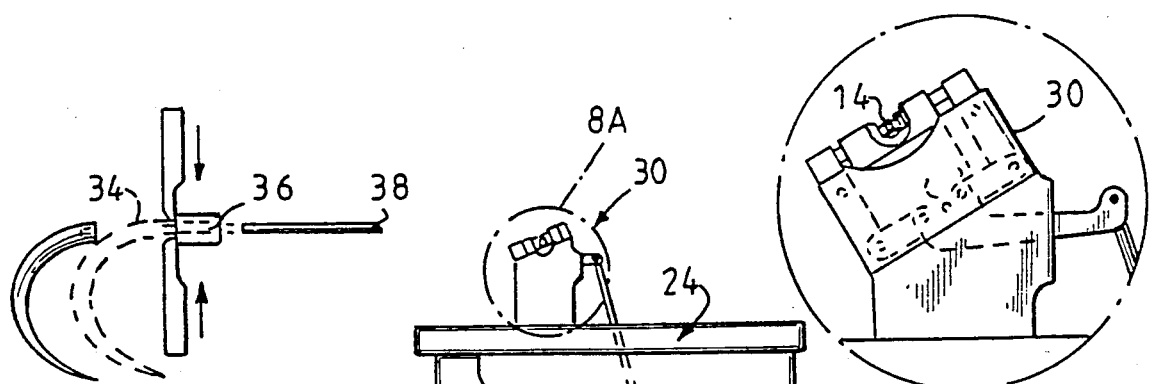
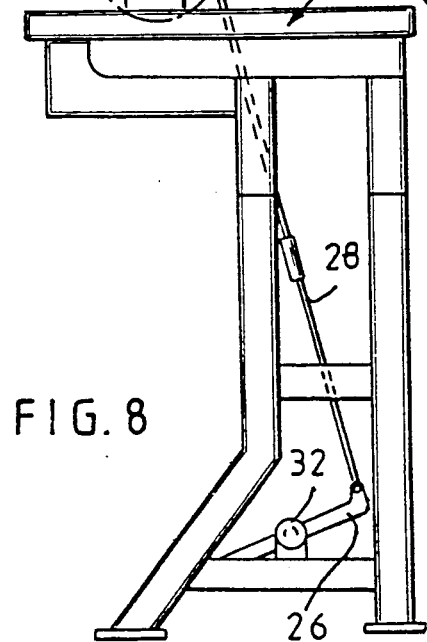
FIG.9  FIG.8A
FIG.8

APPARATUS FOR ATTACHING SURGICAL SUTURE COMPONENTS

BACKGROUND OF THE INVENTION

1. Field of the Invention

The present invention relates to surgical sutures and their production. In particular, the invention relates to surgical sutures and apparatus for the attachment of surgical needles to surgical sutures.

2. Description of Related Art

In the past, surgical needles with an eye for reception of the suture have been used. As in conventional sewing, the thread is sometimes doubled through the eye of the needle. The doubled end of the thread in the eye must pass through tissues during use, which enlarges the opening made in the tissue. This leads to loss of tightness and increased trauma. Due to this problem, there has been a trend towards eyeless needles in which the end of the suture is attached to the needle so that the suture is pulled through the tissue thus minimizing the opening and causing a minimum of trauma.

The most common surgical suture of this type is a single-use needle of appropriate size and shape which is crimped to the end of the suture, so that the needle is used once and then discarded. The attachment can be accomplished by use of a "drilled end" needle; that is, one in which a concentric aperture is formed in the end of the needle in which the suture is placed and the needle crimped around the suture. Alternatively, a "flanged" needle may be utilized in which a U-shaped channel is stamped into the end of the needle with the ends of the "U" being crimped about the suture to hold the suture together.

The attachment must be one which is: predictably secure; causes a minimum of damage to tissue; is convenient for the using surgeon; permits sterilization; and entails reasonable costs. In addition, the attachment must withstand the rigors of manufacture, sterilization, storage, shipment and use.

During use, it has been found that upon completion of the stitching procedure by the surgeon, it is convenient for the surgeon to be able to readily detach the needle from the suture thus permitting the end of the suture to be tied or otherwise secured. The needle may thereafter be removed from the work area so as to avoid harm to the patient, surgeon and other personnel. Cutting the suture with scissors or a scalpel is a convenient method of disengaging the needle but requires an extra instrument and an extra manipulation.

More recently, techniques have been developed to attach the suture to the needle in a manner which permits the surgeon to readily separate the components by merely tugging at the needle at the end of the stitching procedure.

The pull required for tugging the needle from the suture is referred to in the U.S. Pharmacopeia as "needle-attachment" or "testing the security of attachment of eyeless needles to sutures". For convenience, the term "pull-out" is used.

Experience and testing procedures have determined that the pull-out must be at a sufficiently high value that the suture may be placed without risk of the needle becoming detached from the suture during placement; and yet it must pull-out at a value far below the breaking strength of the suture and will predictably pull-out before the suture breaks. In addition, the suture must pull-out at a value which is reasonably exertable upon the needle by the surgeon at the time of use.

Conventional crimp operations are difficult to control. Usually a crimp is created between several dies which close to a fixed gap. Any variation in: the crimping dies, the needle size, the hole size, or the suture size alters the degree of crimp. However, with such techniques, the variation can be larger than is acceptable in the manufacture of controlled release or controlled pull-out sutures.

The conventional crimping method requires that the back end of the needle be struck with two half moon shaped dies. The needle is then rotated 90° and the dies are arranged to strike the needle a second time. In effect, the first strike changes a round hole into one of eliptical shape, i.e., major and minor axes. The act of rotating the needle 90° and repeating the operation to some extent, causes the minor axis to become its counterpart, and the major axis to become the minor axis thereby completing the attachment in a relatively uniform manner. The effect of this procedure is to distort the end of the needle thereby causing it to lose its symmetry. This last mentioned disadvantage results in corresponding assymmetry of tissue apertures during use.

The diameter of the suture, the diameter of the needle, the concentricity of the aperture in the needle, the outside diameter of the needle, the braid size of the suture, coating material, time and concentration of baths, and drying conditions are all extremely critical in predicting and controlling the pull-out force. In addition to size effects, the surface smoothness of the suture and the needle aperture, and lubricants on either components affect the pull-out values. The conventional method of crimping, as described, underscores many of these parametric inconsistencies and necessarily utilizes multiple hits to overcome these process variabilities.

To date, techniques devised for connecting such suture components in a manner to perform within the preferred guidelines are not effective in maintaining needle symmetry and uniformity of dimensions, particularly with a single hit. The present invention avoids the aforementioned disadvantages and provides a die and a method for attaching surgical sutures to needles in a controlled manner while retaining the symmetry of the needle, all with less time and expense.

SUMMARY OF THE INVENTION

The present invention relates to a novel split ring die for attaching the components of surgical sutures which avoids the aforementioned disadvantages of known techniques while providing suture connections which perform within the desired predetermined parameters. Almost perfect symmetry of the attaching suture needle is maintained.

The novel attaching dies are used to attach a suture either in the form of a braid or monofilament, to a drilled end needle. The die is typically used in a suture attaching machine to attach a suture to a drilled end surgical needle.

The novel split ring die provides an improved method of crimping surgical needles to sutures. The novel split ring shape provides a more uniform and quicker swage than obtainable using conventional attaching dies.

The invention provides two very significant improvements when compared to conventional dies. A single hit instead of two or more is used to develop the compression or swage forces while a uniquely defined space within each die provides for reception and collection of superfluous material caused by swaging action. This feature improves the manufacturing economics and reliability of the attaching process. Test reports confirm that predictable pull-out forces are achieved in a convenient and controlled manner using the novel split ring shape die of the present invention. Further, the needle symmetry is maintained in a much improved fashion. The improved needle symmetry is a benefit to the surgeon and the manufacturer.

In a broader sense, the invention relates to an apparatus for attaching two members, at least a first member having a generally cylindrical outer portion defining an elongated aperture having a generally circular cross-section, the second member including a generally elongated end portion of generally circular cross section corresponding in dimension to the elongated aperture of the first member. A pair of dies are provided, each having a pair of generally arcuate spaced surface portions corresponding in dimension and configuration to the generally cylindrical outer surface portion of the first member. The space defines a relief zone between the pair of arcuate spaced inner surface portions such that when the second member is positioned within the aperture of the first member and the dies are respectively positioned about the corresponding portion of the first member with the generally arcuate surface portions facing the first member, applying impact force to the dies to displace the dies toward each other will cause crimping of the first member with respect to the second member so as to attach the members while portions of material forming part of the first member adjacent the stricken area are permitted to be deformed and to collect within the relief zones between the pairs of arcuate surface portions.

A pair of dies according to the present invention are preferably adapted for use in attaching a surgical needle to a surgical suture. Such sutures are typically of suture materials such as silk, nylon, linen, cotton, polyethylene, polypropylene, stainless steel, natural materials such as catgut, and synthetic polymers having glycolic acid ester linkages subject to hydrolytic degradation to non-toxic, tissue compatible absorbable components, including polyglycolic acid. The surgical suture is generally made from a material which is braided, twisted or monofilament. The needle is typically of stainless steel of the drilled end type. Typically, the swaging dies are of a hardened material such as tungsten carbide, and high speed steels.

In the preferred embodiment the apparatus of the invention is used for attaching a surgical needle having a generally cylindrical outer portion defining an elongated aperture having a generally circular cross-section and a suture having a generally elongated end portion of generally circular cross-section corresponding in dimension to the elongated aperture of the first needle. A pair of dies are provided, each having a pair of extensions spaced apart from each other and each defining a generally circular surface portion for swaging corresponding in dimension and configuration to the generally cylindrical outer surface portion of the needle. The space between the extensions defines a relief zone between the pair of extensions and is of configuration and dimension sufficient such that when the suture is positioned within the aperture of the first needle and the dies are respectively positioned about the corresponding portion of the needle, the application of impact force to the dies will cause crimping of the needle with respect to the suture so as to attach the suture and the needle while portions of material forming part of the needle adjacent the stricken area are permitted to be deformed and to collect within the relief zones defined between the extensions and pairs of arcuate surface portions.

A method is disclosed for attaching a surgical needle having a generally cylindrical outer portion and defining an elongated aperture having a generally circular cross-section, and a suture having a generally elongated end portion of generally circular cross-section corresponding in dimension to the elongated aperture of the needle. The method comprises configuring a pair of dies such that each has a pair of extensions spaced apart from each other and defining a generally circular surface portion corresponding in dimension and configuration to the generally cylindrical outer surface portion of the needle, positioning an end portion of the suture within the elongated aperture, positioning the pair of dies adjacent the corresponding cylindrical portion of the needle with the generally circular surface portions facing the generally cylindrical outer portion of the needle, applying inward force to the dies to displace the dies toward each other causing the generally circular surfaces of the dies to engage the surface portion of the needle to thereby cause crimping of the needle and reduction of the average dimension of the aperture defined thereby. The space between the pairs of extensions of each die is configured and dimensioned to permit deformed material of the needle to collect therewithin so as to facilitate attachment of the needle and the suture without distortion of the needle portions adjacent thereto.

According to the method of the invention the needle may be detachably attached to the suture so as to be readily separated as mentioned, by a quick tug provided by the surgeon. Alternatively, the needle may be more firmly attached to provide a "non-detachable" suture in which case the suture may be separated from the needle in a more conventional manner, by cutting with scissors or scalpel.

BRIEF DESCRIPTION OF THE DRAWINGS

Preferred embodiments of the invention are described hereinbelow with reference to the drawings wherein:

FIG. 7 is a front view of an apparatus with which the split ring dies according to the present invention may be utilized to attach a suture to a needle by crimping;

FIG. 8 is a side view of the apparatus shown in FIG. 7;

FIG. 8A is an exploded view illustrating the split ring dies of the present invention mounted in the apparatus of FIG. 7 for attaching a suture to a needle;

FIG. 9 is an exploded side view of a pair of split ring dies constructed according to the present invention positioned to attach a suture to a curved needle.

DETAILED DESCRIPTION OF THE PREFERRED EMBODIMENTS

Figure 1:
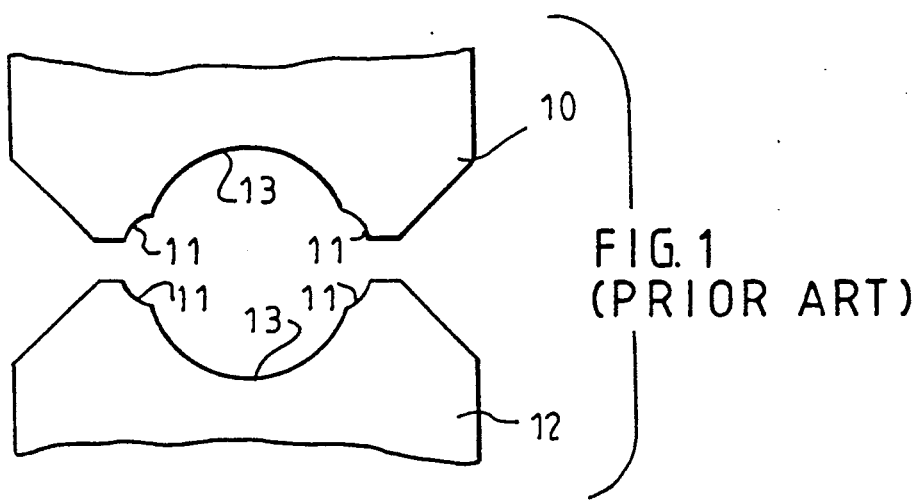
FIG. 1 is a plan view of a pair of conventional dual lap-overlap semi-circular shaped dies.

Referring initially to FIG. 1 there is illustrated a pair of conventional "lap-overlap" dies 10, 12 of the type utilized to attach a suture to a surgical needle. The working surfaces of the dies are shown at 13 and are each generally semi-circular in shape. The working surface of each die 10 shown at 13 is a "lap" region and has adjacent arcuate corner portions 11—designated as "overlap" regions—to receive limited amounts of excess needle material overflowing during the crimping process. The overlap regions are of lesser radii than the lap region as shown and are not concentric therewith as shown. The lap region is configured and dimensioned to receive the elongated apertured rear end portion of a surgical needle between them.

To attach a needle to a suture, the dies are positioned within an apparatus as will be described hereinbelow. The apparatus is arranged to cause both dies to simultaneously move toward each other and strike the needle while it is positioned between them. This causes the needle to become elliptical in cross-section by portions of metal deforming into regions 11. This process reduces the average cross-sectional dimension of the opening. Once the dies are impacted toward each other, they are separated and the needle is rotated 90°. The dies are then struck once again and the attachment is completed. In essence, the first strike causes the circular aperture in the needle to become elliptical. The second strike completes the attachment and reverses the distortion imparted to the needle. In certain instances still additional hits are required to secure the suture to the needle. This procedure necessitates at least a dual step attachment which in turn requires additional time and labor.

Figure 2:
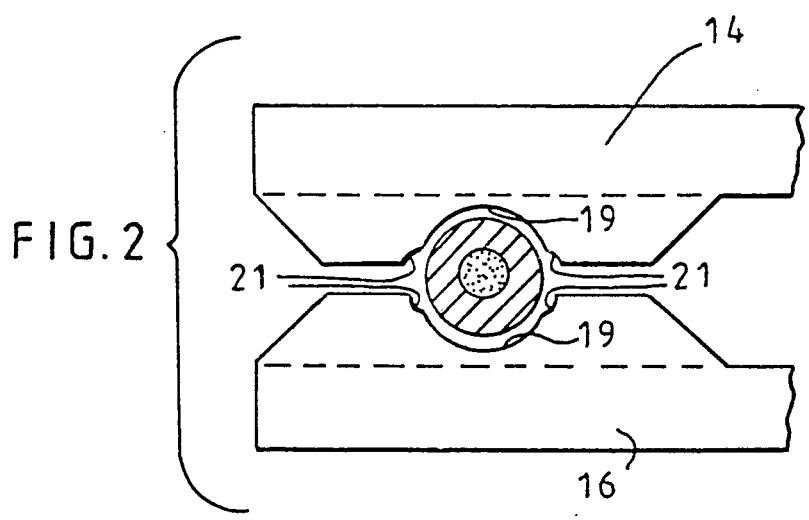
FIG. 2 is a plan view of a pair of split ring swaging dies according to the present invention with a needle and suture positioned therebetween for attachment.
Figure 3:
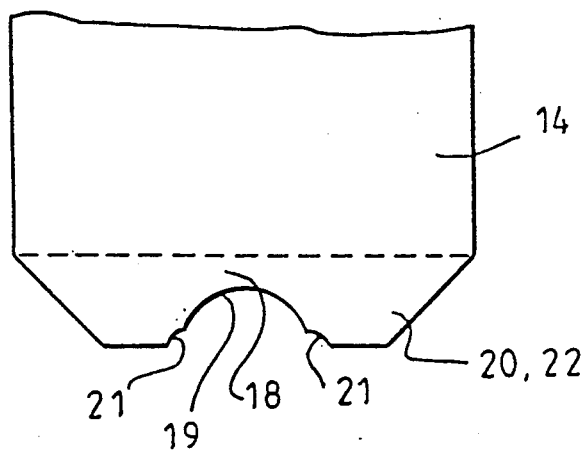
FIG. 3 is an enlarged plan view of a portion of one of the split ring dies of FIG. 2.
Figure 4:
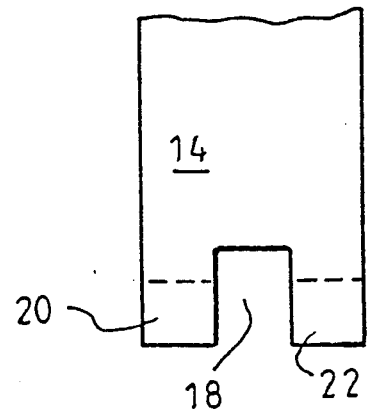
FIG. 4 is an elevational side view of the split ring die shown in FIG. 3.

Referring now to FIGS. 2-4, there is illustrated a pair of split ring dies 14, 16 constructed according to the present invention. Each die is configured to have a semi-circular opening 19 which, when combined with the other die of the pair, forms a complete circular opening for reception of an elongated apertured needle of circular cross-section.

Figure 5:
FIG. 5 is a photomicrograph of an end view of a needle with suture removed illustrating the effects of the crimping attachment accomplished by a pair of split ring dies according to the present invention.
Figure 6:
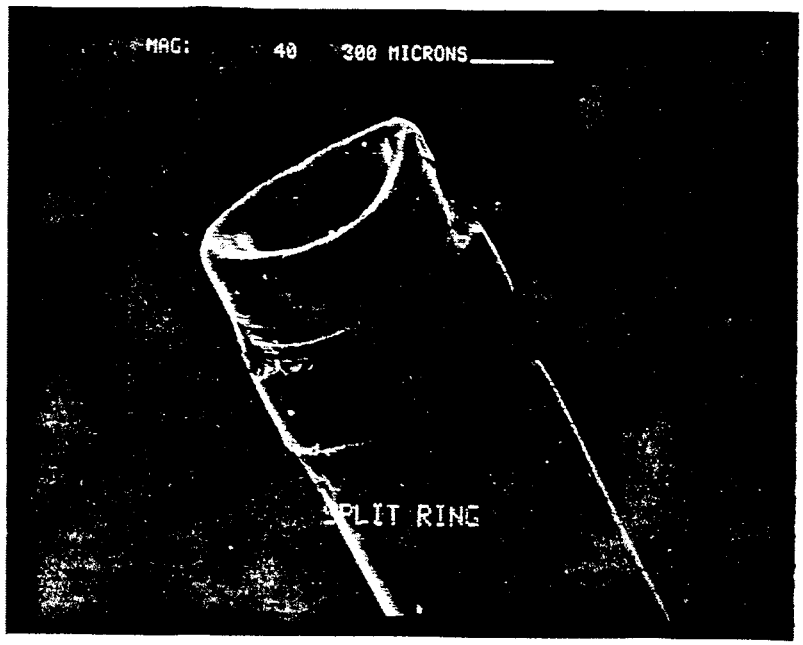
FIG. 6 is a photomicrograph illustrating a perspective view of the "crimped" needle shown in FIG. 5, and the effects of the dies on the surface of the needle.

As shown in FIGS. 2-4 and particularly in FIG. 4 by the representative die 14 of FIG. 2, the die of the present invention has a channel 18 defined between two extensions in the form of depending sections 20, 22 of the die. Preferably the first section 20 is of a thickness equal to the thickness of the rear section 22 as shown in FIG. 4. Further, each section 20, 22 may be equal in thickness to themselves and to the thickness of channel 18. In other words, the thickness of each section 20, 22 and that of channel 18 may be approximately ⅓ of the total thickness of the die as shown in FIG. 4. The channel is provided to relieve needle material being swaged by the die when a pair of the dies are caused to strike a needle positioned within the circular shaped opening as described above. Thus, any material which is stricken by sections 20, 22 and engaged by swaging surfaces 19, will readily accumulate by a swaging action into the relief zone provided by channel 18 in the dies as well as into the overlap area 21. Simultaneously therewith, the apertured portion of the needle will be effectively crimped and attached to the suture by the physical reduction of the dimension of the aperture surrounding the suture. Moreover, the needle will retain its circular symmetry in the area of suture attachment and the attachment will be completed in a fraction of the time normally required in the prior art. A circumferential ridge will form about the outside of the needle in the area of the crimp as shown in FIGS. 5 and 6. The present invention contemplates the provision of channel 18 with or without the lap-overlap relief zones 11.

Figure 10:
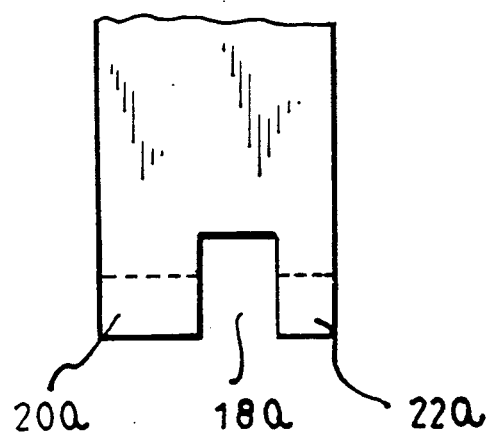
FIG. 10 is a view of an alternative embodiment of a split ring die constructed according to the invention.

FIG. 10 illustrates an embodiment of the invention in which the widthwise dimension of each extension of the dies are unequal. Extension 20a is thicker than extension 22a and the space 18 therebetween is of width approximately between the thickness of the extensions.

Referring now to FIGS. 5 and 6, two photomicrographs are shown of actual surgical needles which have been struck by the split ring dies constructed according to the invention. In FIG. 5 the needle is of the curved type In FIG. 6, the needle is a straight needle. In each example a raised circumferential ridge of material swaged and deformed away from the area of the strike is evident.

Referring now to FIGS. 7 and 8 there is shown an exemplary apparatus 24 on which sutures may be attached to needles utilizing a pair of the split ring dies of the present invention. The apparatus 24 shown is manufactured and marketed as model 6A Suture Attaching Machine by B.G. Sulzle, Inc., Syracuse, N.Y. Other comparable machines suitable for attaching sutures may be utilized with the dies of the present invention.

The suture attaching machine 24 as illustrated in FIG. 7 includes a table 25 having treadle 26 which is foot operated and connected via treadle rod 28 to suture press 30. The treadle 26 is mounted for pivotal movement on pivot rod 32.

Referring now to FIG. 8 there is shown a side view of the apparatus shown in FIG. 7. The suture press 30 is encircled and is shown in enlarged form in FIG. 8A. As can be seen in FIG. 8A, the pair of split ring dies 14 which are constructed according to the invention are positioned within the jaws of the suture press 30 and arranged to be stricken against a needle with the suture in position as shown in FIG. 9.

The needle 34 shown in FIG. 9 is of a curved type having a straight rear end portion which defines an elongated aperture 36 dimensioned for reception and attachment to an appropriately sized suture 38. The needle 34 is supported on a guide support having a "V shaped" guide channel which positively determines and positions the needle location and orientation as shown. Thereafter, appropriate adjustments are made to predetermine the strike force to be transmitted to the needle and suture as may be appropriately calculated to obtain a predetermined pull-out force. The treadle is depressed to cause the dies to strike the needle.

It will be readily appreciated that the dies of the present invention are particularly advantageous in that all types of sutures may be readily attached to needles having an aperture in their blunt end, i.e., drilled end needles, utilizing a single strike force thereby avoiding the need to provide "double-hit" attachment as necessary with prior art dies. This procedure provides a suture having a needle which is symmetrical and unaffected by the distorting forces provided by dies and procedures of the prior art. Moreover, the single-hit attachment procedure provides consistent and controlled attachment of the suture and the needle which additionally reduces the time and effort to complete the attachment. Die life is increased, rejected needle/suture attachments are reduced, and attachment time is reduced. As a result the cost of producing a surgical suture is sizably reduced.

Examples of comparisons of pull-out provided by the present invention "split ring" die) and prior art ("control") attachments are provided in the following table.

TABLE I

| Split Ring vs. Controls Size 0 | | | | |
|---|---|---|---|---|
| | \multicolumn{4}{c}{Pull-Out Force} |
| | Pre-Steriliz | | Post-Steriliz | |
| Control 1 VICRYL brand SYNTHETIC absorbable suture (Prior Art Double-Hit) | (No Data) | | n = 10 | 2.8 kgs |
| Control 2 Monofilament nylon suture (Prior Art Double-Hit) | n = 10 | 1.8 kgs | n = 10 | 1.8 kgs |
| Control 3 Braided synthetic absorbable suture (Prior Art Double-Hit) | n = 5 | 2.6 kgs | n = 5 | 2.9 kgs |
| Split Ring Die Braided synthetic absorbable suture | n = 15 | 3.2 kgs | n = 8 | 3.1 kgs |
| Split Ring Monofilament nylon suture | n = 11 | 3.3 kgs | n = 15 | 2.9 kgs |

The foregoing table clearly illustrates and underscores the advantages of the present invention in providing consistent and controlled needle/suture attachments using a single hit In fact, in each case the attachments made according to the invention exhibited pull-out forces to separate the suture from the needle at least equal to those of the prior art double-hit (or multiple hit) attachments. In each instance the attachment of the present invention was accomplished by a single-hit procedure, in a fraction of the time, and provided a strike zone in the needle free of distortions or cold working effects. The last mentioned adverse effect can be expected with prior art needle suture attachment methods.

The swaging dies of the present invention may be utilized with all types of needles such as curved needles, straight needles, or the like, provided they have an elongated aperture on their end portion for receiving the suture. Sutures usable with the present invention include silk, nylon, linen, cotton, polyester, polypropylene, stainless steel, natural materials such as catgut, synthetic polymers having glycolic acid ester linkages subject to hydrolytic degradation to non-toxic tissue compatible absorbable components, including polyglycolic acid. The sutures may be monofilamentary or braided, absorbable or non-absorbable. The dies of the present invention are preferably constructed of a hardened material such as tungsten carbide However, it should be understood that all materials suitable for such die construction may be used, provided the geometric and configurational parameters taught by the present invention are met.

We claim:

1. Apparatus for attaching two members, at least a first elongated member having a generally arcuate outer surface portion and defining an elongated aperture of generally arcuate cross-section, and a second member including at least an end portion of generally arcuate outer configuration corresponding in configuration and dimension to the elongated aperture of the first member, which comprises a pair of dies each having a pair of extensions having a space therebetween and correspondingly defining a pair of generally arcuate spaced surface portions corresponding in dimension and configuration to the generally arcuate outer configuration of the first member, said space defining a relief zone between said pair of extensions such that when said end portion of the second member is positioned within the aperture of the first member and said dies are positioned about the corresponding portion of the first member with said pair of spaced generally arcuate surface portions of a first die facing the first member on one side, and said pair of spaced generally arcuate surface portions of said second die facing the first member on the opposite side and inward force is applied to said dies to displace said dies toward each other, said generally arcuate surface portions of said dies engage the first member and cause crimping thereof while portions of material forming part of the first member adjacent the areas subject to said inward force are permitted to be deformed and to collect within said adjacent relief zones defined by said space between each of said pair of spaced extensions of said dies so as to attach the members while maintaining substantially the same arcuate cross-sectional character of the outer surface portion of the first member thereby crimped.

2. Apparatus for attaching two members, at least a first member having a generally cylindrical outer surface portion and defining an elongated aperture having a generally circular cross-section, the second member including a generally elongated end portion of generally circular cross-section corresponding in dimension to the elongated aperture of the first member, which comprises a pair of dies each having a pair of generally arcuate surface portions and having a space therebetween and corresponding in dimension and configuration to the generally cylindrical outer surface portion of the first member, said space defining a relief zone channel between said pair of arcuate spaced surface portions of each die such that when the second member is positioned within the aperture of the first member and said dies are respectively positioned about the corresponding portion of the first member with said pair of spaced arcuate surface portions of a first die facing the first member and said pair of spaced arcuate surface portions of said second die facing the first member on the opposite side, applying impact energy to said dies will cause said dies to engage and crimp the first member with respect to the second member by forces distributed substantially uniformly about the second member so as to maintain substantially the same cylindrical cross-sectional character of the first member throughout the portion crimped by said dies so as to attach the members while portions of material forming part of the first member adjacent the area engaged by said dies are permitted to be deformed and to collect within said relief zones between said pairs of arcuate surface portions.

3. Apparatus for crimping a cylindrical member for attachment to an elongated member of generally circular cross-section, the cylindrical member defining a generally elongated aperture of widthwise dimension similar to the outer widthwise dimension of at least an end portion of the elongated member, which comprises a pair of dies, each having a pair of arcuate surface portions having a space therebetween and adapted to receive and collect material forming part of the cylindrical member when said dies are positioned about the members with a pair of said spaced arcuate surface portions of a first die facing the cylindrical member on one side and a pair of spaced arcuate surface portions of said second die facing the cylindrical member on the opposite side and said first member is crimped with force sufficient to reduce the widthwise dimension of said elongated aperture of said cylindrical member sufficient to thereby attach the members while causing material forming part of the cylindrical member to be swaged and collected within said spaces between said arcuate surface portions of said dies, whereby attachment of the members is accomplished by crimping without substantial deformation or distortion of the cross-sectional dimensions of the first member and maintaining substantially the same cross-sectional character of the first member in the portion crimped by said dies.

4. The apparatus according to claim 3 wherein said pair of dies are dimensioned and adapted for attaching a surgical needle to a surgical suture made of at least one of suture materials such as silk, nylon, linen, cotton, polyester, stainless steel, polypropylene, natural materials such as catgut, and synthetic polymers having glycolic acid ester linkages subject to hydrolytic degradation to non-toxic, tissue compatible absorbable components, including polyglycolic acid.

5. The apparatus according to claim 4 wherein said pair of dies are dimensioned and adapted for attaching a surgical suture in the form of a braided, or twisted multifilament or a monofilament to a cylindrical member in the form of a surgical needle.

6. The apparatus according to claim 5 wherein said dies are preferably of a hardened material such as tungsten carbide or high speed steel.

7. Apparatus for attaching a surgical needle having a generally cylindrical end portion defining an elongated aperture having a generally circular cross-section and a suture having a generally elongated end portion of generally circular cross-section corresponding in dimension to the elongated aperture of the needle, which comprises a pair of dies each having a pair of extensions having a space therebetween and defining a circular surface portion corresponding in dimension and configuration to the generally cylindrical outer surface portion of the needle, said space between said pair of extensions defining a relief zone and being of configuration and dimension sufficient such that when the suture is positioned within the aperture of the needle and said dies are respectively positioned about the corresponding portion of the needle, applying impact force to said dies will cause said dies to engage and crimp the needle with respect to the suture so as to attach the suture and the needle by forces distributed substantially uniformly about the suture, while portions of material forming part of the needle adjacent the areas engaged by said dies are permitted to be deformed and to collect within said relief zones defined between said pairs of circular surface portions in a manner to maintain substantially the same generally circular cross-sectional character throughout the crimped portion of the needle.

8. The apparatus according to claim 7 wherein each said circular surface portion extends from a first portion of a die face to a second portion of said die face.

9. The apparatus according to claim 8 wherein each said circular surface portion of each said die face defines an overlap material relief zone, said overlap material relief zone being comprised of an arcuate surface portion of radius less than the radius of said circular die surface and intersecting said circular die surface.

10. The apparatus according to claim 9 wherein each said extension is approximately the same widthwise dimension.

11. The apparatus according to claim 10 wherein each extension is approximately the same widthwise dimension and said space therebetween is approximately the same widthwise dimension as each extension.

12. The apparatus according to claim 9 wherein each said extension is of different widthwise dimension.

13. The apparatus according to claim 12 wherein each first extension is of a greater widthwise dimension than the second extension and the space therebetween is of widthwise dimension between the widthwise dimension of each extension.

* * * * *